United States Patent

Hirota et al.

[11] Patent Number: 5,987,972
[45] Date of Patent: Nov. 23, 1999

[54] METHOD FOR DETECTION OF SOLID PARTICLES IN FLUID AND PARTICLE SENSOR USED IN SAID METHOD

[75] Inventors: Toshikazu Hirota, Kuwana; Kazuyoshi Shibata, Mizunami; Yasuhito Yajima, Haguri-gun, all of Japan

[73] Assignee: NGK Insulators, Ltd., Japan

[21] Appl. No.: 09/047,118

[22] Filed: Mar. 24, 1998

[30] Foreign Application Priority Data

Aug. 20, 1997 [JP] Japan .................................. 9-223533

[51] Int. Cl.$^6$ ............................ G01N 15/06; G01N 29/02
[52] U.S. Cl. ........................ 73/61.75; 73/61.49; 310/338
[58] Field of Search ................. 73/24.01, 24.03, 73/24.06, 28.01, 53.01, 53.05, 53.07, 61.41, 61.42, 61.49, 61.71, 61.75, 61.79; 310/338

[56] References Cited

U.S. PATENT DOCUMENTS 5,698,931  12/1997  Shibata et al. .......................... 310/338
5,747,671   5/1998  Hirota et al. ........................... 73/61.75
5,825,119  10/1998  Shibata et al. .......................... 310/338
5,877,411   3/1999  Namerikawa et al. ............. 73/61.49 X

FOREIGN PATENT DOCUMENTS 7-301594  11/1995  Japan .

Primary Examiner—Daniel S. Larkin
Attorney, Agent, or Firm—Wall, Marjama, Bilinski & Burr

[57] ABSTRACT

A method for detecting the solid particles contained in a fluid, by the use of a particle sensor having a flow path of a fluid, having a fluid inlet and a fluid outlet, and a sensor element provided in the flow path, which comprises (a) a vibrating section having such a mass that is sensitive to the collision of solid particles contained in the fluid, with the vibrating section and (b) a detecting section for detecting the vibration of the vibrating section caused by the collision and converting the vibration to electric signals. The method includes steps of: passing a fluid to be examined, through the particle sensor, selectively detecting, from the electric signals outputted from the particle sensor, an electric signal portion having particular frequencies ranging from 1/50 to 10 times the primary resonance frequency of the sensor element, measuring the maximum amplitude of the electric signal portion, comparing the maximum amplitude measured above, with a given value predetermined with the particle sensor based on (1) the maximum amplitude of a portion of the electric signals caused by the collision of solid particles contained in a fluid, having the above particular frequencies and (2) the maximum amplitude of a portion of the electric signals caused by the turbulent flow of the same fluid containing no solid particles, having the above particular frequencies, and judging, depending upon the result of the above comparison, whether or not the electric signals outputted from the particle sensor with the fluid to be examined have been caused by the collision of solid particles with the particle sensor.

8 Claims, 7 Drawing Sheets

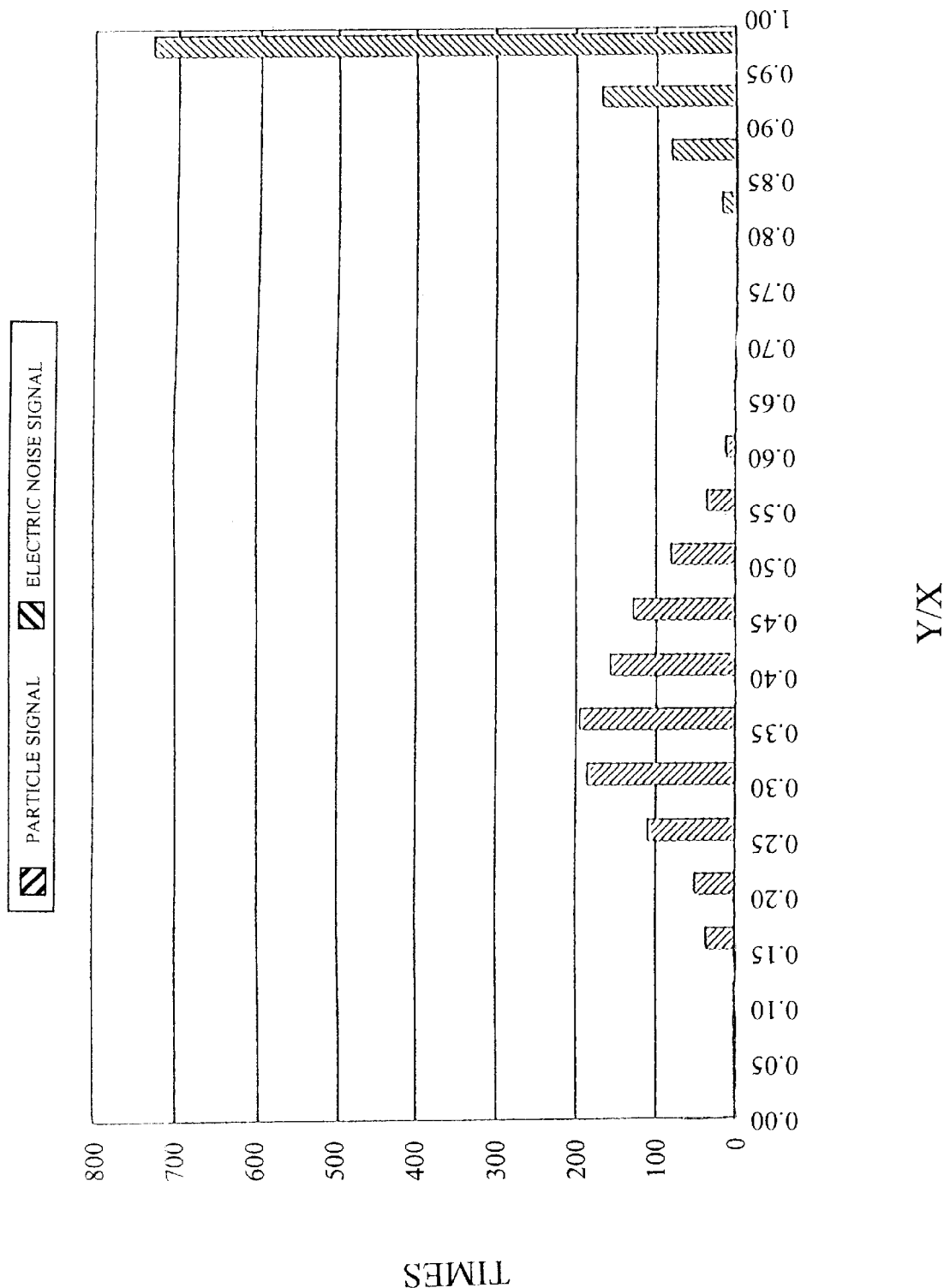

METHOD FOR DETECTION OF SOLID PARTICLES IN FLUID AND PARTICLE SENSOR USED IN SAID METHOD

BACKGROUND OF THE INVENTION

1. Field of the Invention

The present invention relates to a particle sensor for detecting the solid particles contained in a fluid.

2. Description of Related Art

When solid particles are present in a fluid (a liquid or a gas), it is necessary in some cases to detect presence of those the solid particles. Detection of such solid particles is particularly important when the solid particles present in the fluid detrimentally affect the intended action of the fluid.

Lubricating oils (e.g. engine oils) are used in internal combustion engines of automobiles or heavy machinery in order to reduce the frictional resistance and abrasion of the rotating surfaces and sliding surfaces of the engines. Operation of such internal combustion engines generates solid particles (e.g. metal fine particles) caused by abrasion, and the solid particles are taken into the lubricating oils and accelerate the abrasion of the rotating surfaces and sliding surfaces. The solid particles, etc. present in the lubricating oils are ordinarily removed by the use of a filter, such as oil filter or the like. The condition of the lubricating oils can be monitored by detecting the solid particles present in the lubricating oils.

Hydraulic oils and flushing oils are used in power transmission mechanisms (e.g. transmission), oil hydraulic pipe systems (e.g. oil hydraulic servo valve), rolling, pressing, etc. It is important to control the condition of these oils by detecting the solid particles present in the oils and/or examining the viscosities of the oils.

It is also important to detect the particles suspended in the air or examine their concentration in the air in order to monitor the level of air pollution. Such detection includes detection of the particles suspended in the exhaust gas discharged from a plant, a factory or the like.

For such detection of solid particles present in a fluid, a particles sensor comprising a sensor element using a piezoelectric film is disclosed in Japanese Patent Application Laid-Open (Kokai) No. 7-301594. With this particle sensor, solid particles present in a fluid collide with the detecting section (having a piezoelectric film) of the sensor element or with the vibrating section (mounting the detecting section thereon) of the sensor element, thereby causing the vibrating section and the detecting section to vibrate. The piezoelectric film converts the vibration into electric signals, which are outputted by electrodes holding the piezoelectric film between them.

In detecting solid particles contained in a fluid by the use of a particle sensor such as mentioned above, the vibrating section of the sensor element of the particle sensor is vibrated not only when the solid particles in a fluid collide with the vibrating section but also when the flow of the fluid becomes turbulent as a result, electric signals are outputted from the detecting section of the sensor element. Moreover, electric noise signals may enter the particle sensor from outside.

No method has heretofore been established to clearly distinguish the above-mentioned three kinds of electric signals, i.e. (1) the electric signals caused by the collision of solid particles (the signals are hereinafter referred to as "particle signals"), (2) the electric signals caused by the turbulent flow of fluid (the signals are hereinafter referred to as "turbulent flow signals") and (3) the electric noise signals which may enter the particle sensor from outside (the signals are hereinafter referred to as "electric noise signals"). This is one reason that the detection of solid particles in fluid has been unreliable.

SUMMARY OF THE INVENTION

Hence, the objects of the present invention are to provide a method for detection of the solid particles contained in a fluid, using a particle sensor. This method can distinguish the particles signals output by the sensor from other signals output from the sensor. It is a further object of the present invention to provide a particle sensor suitably used in the above described detection method.

According to the present invention, there is provided a method for detecting the solid particles contained in a fluid, by the use of a particle sensor comprising:

a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals.

According to this method a fluid to be examined is passed through the particle sensor. The from the electric signals outputted from the particle sensor, an electric signal portion having particular frequencies ranging from $\frac{1}{50}$ to 10 times the primary resonance frequency of the sensor element is then selectively detected. Next, the maximum amplitude of said electric signal portion is measured. The maximum amplitude above is then compared with a given value predetermined with the particle sensor based on (1) the maximum amplitude of a portion of the electric signals caused by the collision of solid particles contained in a fluid, having the above particular frequencies and (2) the maximum amplitude of a portion of the electric signals caused by the turbulent flow of the same fluid containing no solid particles, having the above particular frequencies. Depending upon the result of the above comparison, a judgement is made whether or not the electric signals outputted from the particle sensor with the fluid to be examined have been caused by the collision of solid particles with the particle sensor. (This method is hereinafter referred to as the first method.)

According to the present invention, there is also provided a particle sensor comprising: a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals. Particle sensor is provided with a detecting means capable of detecting, from the electric signals outputted from the particle sensor, an electric signal portion having particular frequencies ranging from $\frac{1}{50}$ to 10 times the primary resonance frequency of the sensor element of the particle sensor, and a measuring means capable of measuring the maximum amplitude of the detected electric signal portion. (This particle sensor is hereinafter referred to as the first particle sensor.)

According to the present invention, there is further provided a method for detecting the solid particles contained in a fluid, by the use of a particle sensor comprising: a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals. According to this method a fluid to be examined is passed through the particle sensor. Then from the electric signals outputted from the particle sensor, an electric signal portion having particular frequencies ranging from $1/50$ to 10 times the primary resonance frequency of the sensor element is then selectively detected the maximum amplitude X of said electric signal portion is then measured. From the electric signals outputted from the particle sensor, an electric signal portion having particular frequencies ranging from 2 to 10 times the primary resonance frequency of the sensor element, and measuring the maximum amplitude Y of said electric signal portion, is then selectively detected. When Y/X is equal to or smaller than a given value, a judgement is made whether the electric signals outputted from the particle sensor with the fluid to be examined has been caused by solid particles. (This method is hereinafter referred to as the second method.)

According to the present invention, there is furthermore provided a particle sensor comprising: a flow path of a fluid, having a fluid inlet and a fluid outlet, and a sensor element provided in said flow path, which comprises (a) a vibrating section having such a mass that is sensitive to the collision of solid particles contained in the fluid. With the vibrating section and (b) a detecting section for detecting the vibration of the vibrating section caused by said collision and converting the vibration to electric signals. This particle sensor is provided with a first detecting means capable of detecting, from the electric signals outputted from the particle sensor, an electric signal portion having particular frequencies ranging from $1/50$ to 10 times the primary resonance frequency of the sensor element of the particle sensor. The particle sensor also includes a second detecting means capable of detecting, from the electric signals outputted from the particle sensor, an electric signal portion having particular frequencies ranging from 2 to 10 times the primary resonance frequency of the sensor element, and a measuring means capable of measuring the maximum amplitudes of said two electric signal portions. (This particle sensor is hereinafter referred to as the second particle sensor.)

BRIEF DESCRIPTION OF THE DRAWINGS

FIG. 2(a) is a plan view and FIG. 2(b) is a sectional view taken along the line I—I of FIG. 2(a).

FIG. 9 is a graph showing the results obtained in Example 2.

DETAILED DESCRIPTION OF THE PREFERRED EMBODIMENT

In the first method of the present invention for detecting the solid particles contained in a fluid, it is judged whether the electric signals outputted from the particle sensor used in the method are particle signals or turbulent flow signals, whereby the solid particles contained in the fluid can be detected at a higher accuracy.

The particle sensor used in the first method for detecting the solid particles contained in a fluid comprises: a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals. In this particle sensor, a fluid entering there from the fluid inlet contacts with the vibrating section of the sensor element provided in the flow path and, when the fluid contains solid particles, the solid particles collide with the vibrating section and cause the vibration of the vibrating section. The vibration is converted into electric signals by the detecting section of the sensor element, and the electric signals are outputted to terminal pads or the like. After the contact with the vibrating section, the fluid is discharged out of the particle sensor from the fluid outlet.

Figure 3:
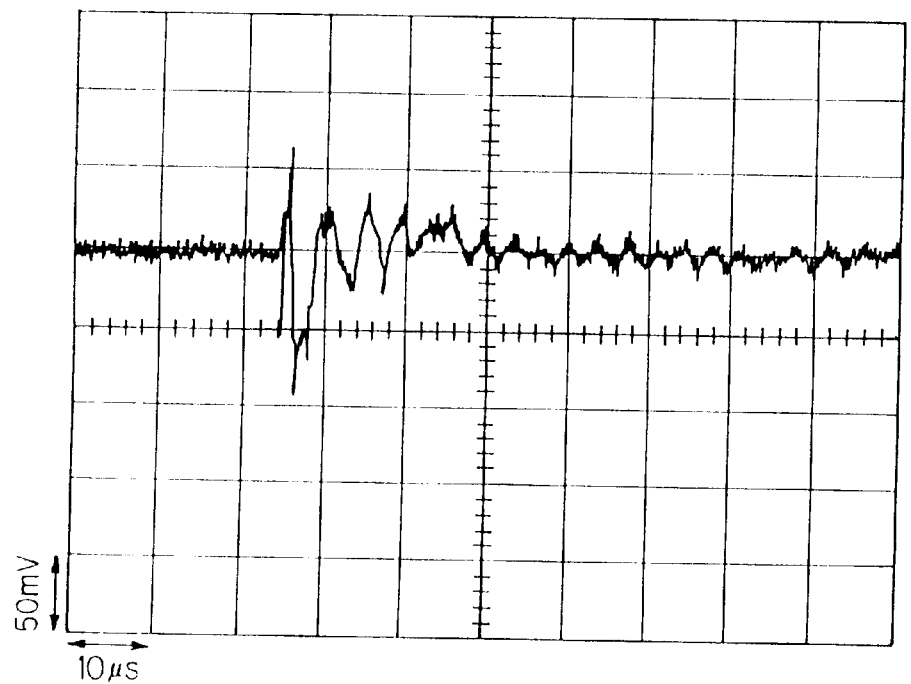
FIG. 3 shows a waveform of the electric signals recorded after passing the electric signals (generated in the detecting section of the sensor element of the particle sensor of FIG. 1 by the collision of solid particles in a fluid, with the vibrating section of the sensor element) through a band-pass filter capable of passing electric signals having frequencies ranging from $1/50$ to 10 times the primary resonance frequency of the sensor element.
Figure 4:
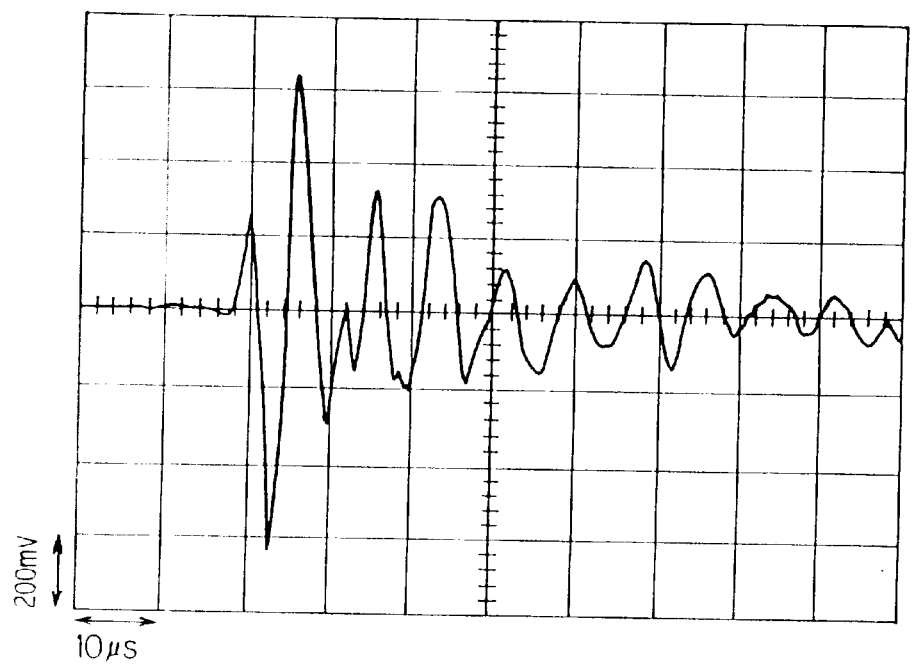
FIG. 4 shows a waveform of the electric signals recorded after passing the electric signals (generated in the detecting section of the sensor element of the particle sensor of FIG. 1 by the hitting of the turbulent flow of a fluid against the vibrating section of the sensor element) through a band-pass filter capable of passing electric signals having frequencies ranging from $1/50$ to 10 times the primary resonance frequency of the-sensor element.

FIG. 3 shows a waveform of the electric signals recorded after passing the particle signals generated in the above particle sensor, through a band-pass filter capable of passing electric signals having frequencies ranging from 1/50 to 10 times the primary resonance frequency of the sensor element of the particle sensor. FIG. 4 shows a waveform of the electric signals recorded after passing the turbulent flow signals generated in the above particle sensor, through a band-pass filter capable of passing electric signals having frequencies ranging from 1/50 to 10 times the primary resonance frequency of the sensor element.

As is clear from the comparison of FIG. 3 and FIG. 4, the maximum amplitude (peak-to-peak) of a portion of the turbulent flow signals having particular frequencies ranging from 1/50 to 10 times the primary resonance frequency of the sensor element of the particle sensor is considerably larger than the maximum amplitude of a portion of the particle signals having the same particular frequencies. This difference in maximum amplitude between the two kinds of signals is utilized in the first method. The reason for utilizing, in the first method, the above two maximum amplitudes each of a signal portion having the above particular frequencies is as follows.

Figure 7:
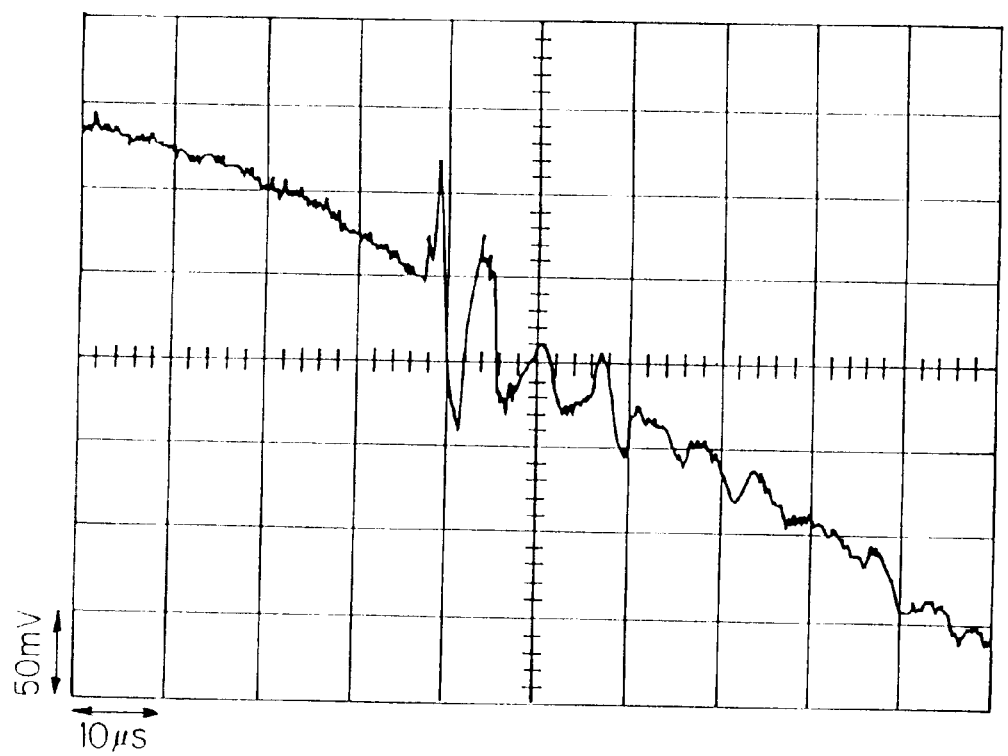
FIG. 7 shows a waveform of the electric signals generated in the detecting section of the sensor element of the particle sensor of FIG. 1 (having no band-pass filter) by the collision of solid particles in a fluid, with the vibrating section of the sensor element, in which waveform the base line of the electric signals is shifted by, for example, the variation of flow rate of fluid.

FIG. 7 shows an example of the waveform of the particle signals outputted from a particle sensor such as mentioned above. As seen in FIG. 7, there may occur a shift of the base line of the signals outputted from a particle sensor, owing to, for example, the variation of flow rate of fluid. This shift of base line makes it difficult to accurately know the maximum amplitude of outputted signals. Since the base line causing a shift generally has frequencies lower than 1/50 of the primary resonance frequency of the sensor element of the particle sensor, elimination of signals having such low frequencies can make the base line constant. High-frequency noises having frequencies higher than 10 times the primary resonance frequency of the sensor element of the particle sensor are also an obstacle for accurately knowing the maximum amplitude of outputted signals. Therefore, it is desirable to eliminate signals having such high frequencies.

As the means capable of eliminating those signals becoming an obstacle for accurately knowing the maximum amplitude of outputted signals and selectively detecting those signals having particular frequencies ranging from 1/50 to 10 times the primary resonance frequency of the sensor element of the particle sensor, there can be mentioned, for example, a band-pass filter capable of passing a signal portion having said particular frequencies.

In the first method, the maximum amplitude of a portion of the electric signals outputted from the particle sensor, having the above particular frequencies is compared with a given value described later. Based on the result of the comparison, it is judged whether or not the electric signals outputted from the particle sensor have been caused by the collision of solid particles with the particle sensor.

Needless to say, the given value mentioned above must be such a value as, by comparing it with said maximum amplitude, the kind of the electric signals giving said maximum amplitude, i.e. particle signals or turbulent flow signals can be ascertained. The given value is determined by measuring the maximum amplitude of particle signals of said particular frequency range and also the maximum amplitude of turbulent flow signals of said particular frequency range, and comparing the two maximum amplitudes.

Determination of the given value is made as follows, for example. First, with the particle sensor used in the first method, particle signals are generated a plurality of times under the same conditions as in actual use of the sensor. From a plurality of the particles signals generated, signal portions having the above-mentioned particular frequencies are selectively detected and the maximum amplitudes of individual signal portions are measured. The largest of these maximum amplitudes is taken as A. Also, with the same particle sensor, turbulent flow signals are generated a plurality of times under the same conditions as in actual use of the sensor. From a plurality of the turbulent flow signals generated, signal portions having the above-mentioned particular frequencies are selectively detected and the maximum amplitudes of individual signal portions are measured. The smallest of these maximum amplitudes is taken as B. When the given value is taken as C, C is determined so as to satisfy the following formula.

$$A \leq C < B$$

The thus-determined C is compared with the maximum amplitude of a portion of the electric signals outputted from the particle sensor (used in the first method), having the above-mentioned particular frequencies. When the comparison indicates that the maximum amplitude is equal to or smaller than C, the electric signals giving said maximum amplitude are judged to be particle signals. Conversely when the maximum amplitude is larger than C, the electric signals giving said maximum amplitude are judged to be turbulent flow signals. This judgement can therefore increase the accuracy of detection of the solid particles contained in a fluid.

For increasing the accuracy of said detection, the times of generation of particle signals and turbulent flow signals for obtaining A and B are preferably as many as possible. The times are desirably, for example, about 1,000 times for respective signals. Also for increasing the accuracy of the detection, the given value C is preferably intermediate between A and B. However, when the times of generation of particle signals for obtaining A are sufficiently many, B need not be measured and A can be regarded as C.

The given value C, which is determined as above, varies depending upon the flow rate of fluid, the sizes of solid particles contained in fluid, etc. In Example 1 shown later, the given value C was specifically determined by applying the first method to the lubricating oil system of a large-sized diesel engine. Also when the first method is applied to other usages, the given value C can be determined in a manner similar to that in Example 1.

Next, description is made on the first particle sensor of the present invention. The first particle sensor has been invented with an aim of effectively carrying out the above-mentioned first method for detecting the solid particles contained in a fluid. The first particle sensor comprises: a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals.

Figure 1:
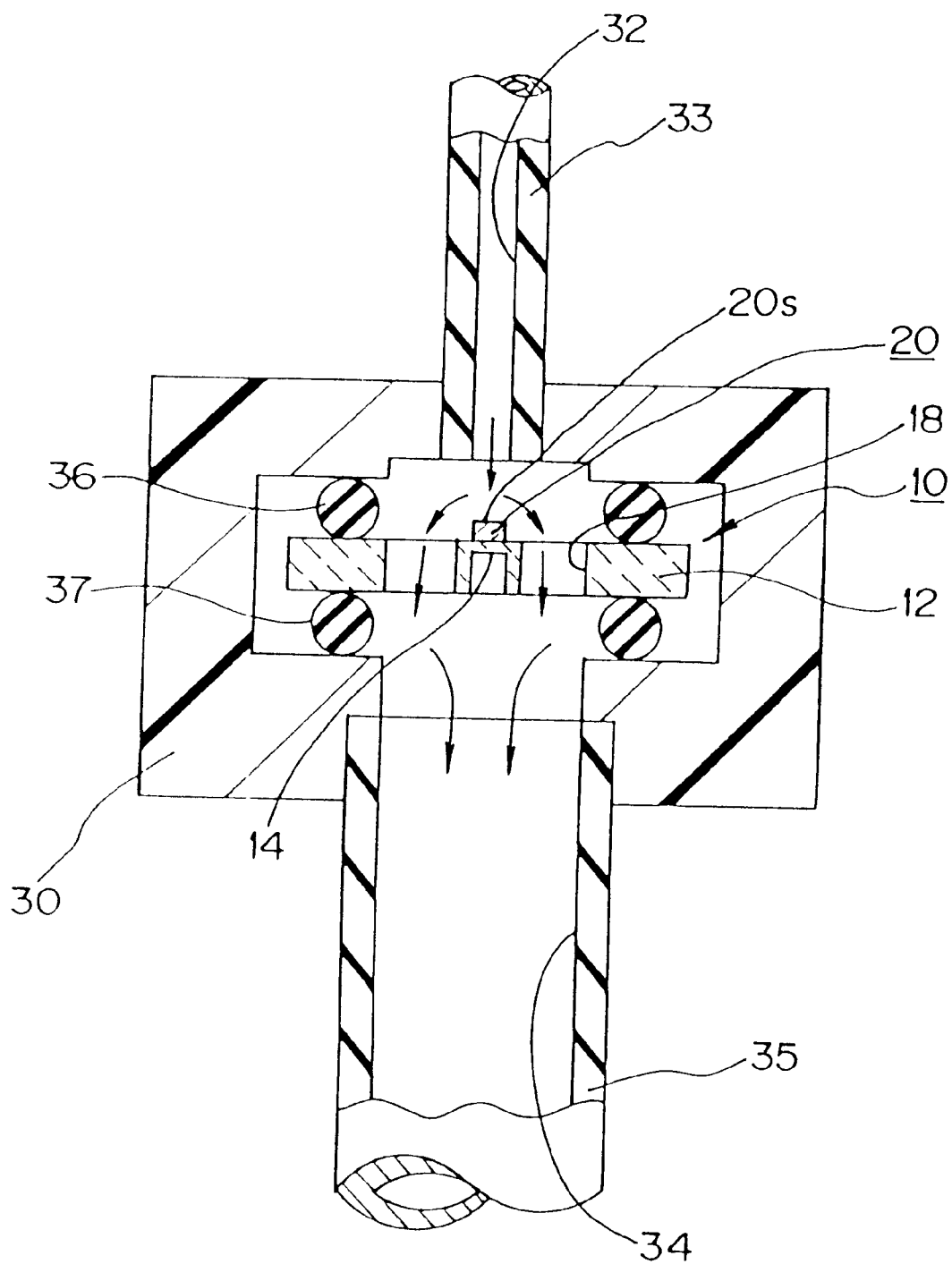
FIG. 1 is a drawing showing an example of the basic structure of the particle sensor according to the present invention.

FIG. 1 shows an example of the basic structure of the first particle sensor. In this basic structure, the flow path of a fluid is constituted by a nozzle 33 forming the inlet 32 of the fluid, a nozzle 35 forming the outlet of the fluid, and a housing 30 to which the nozzles 33 and 35 are fixed and which accommodates a sensor element 10 between the nozzle 33 and the nozzle 35. The sensor element 10 is fixed to the inside of the housing 30 via elastic members 36 and 37 (e.g. o-rings). The means for fixing the sensor element 10 to the housing inside is not restricted to elastic members and may be screws, adhesives, etc.

Figure 2A:
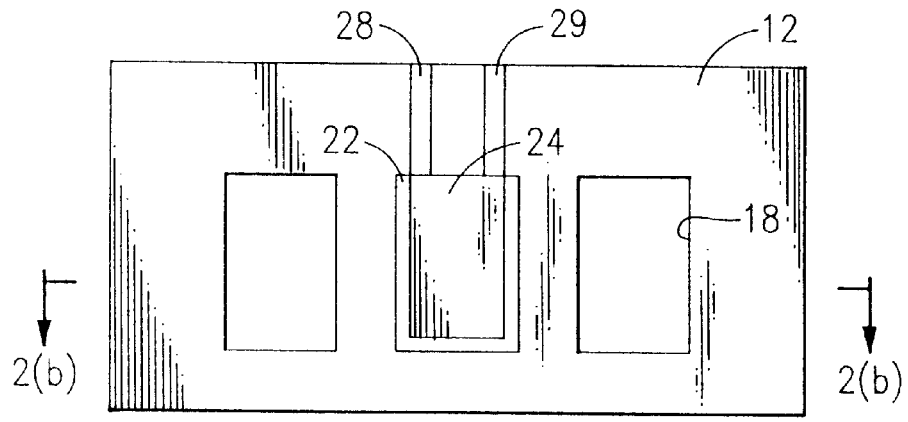
FIGS. 2(a) (b) are drawings showing an example of the sensor element used in the particle sensor of FIG. 1.
Figure 2B:
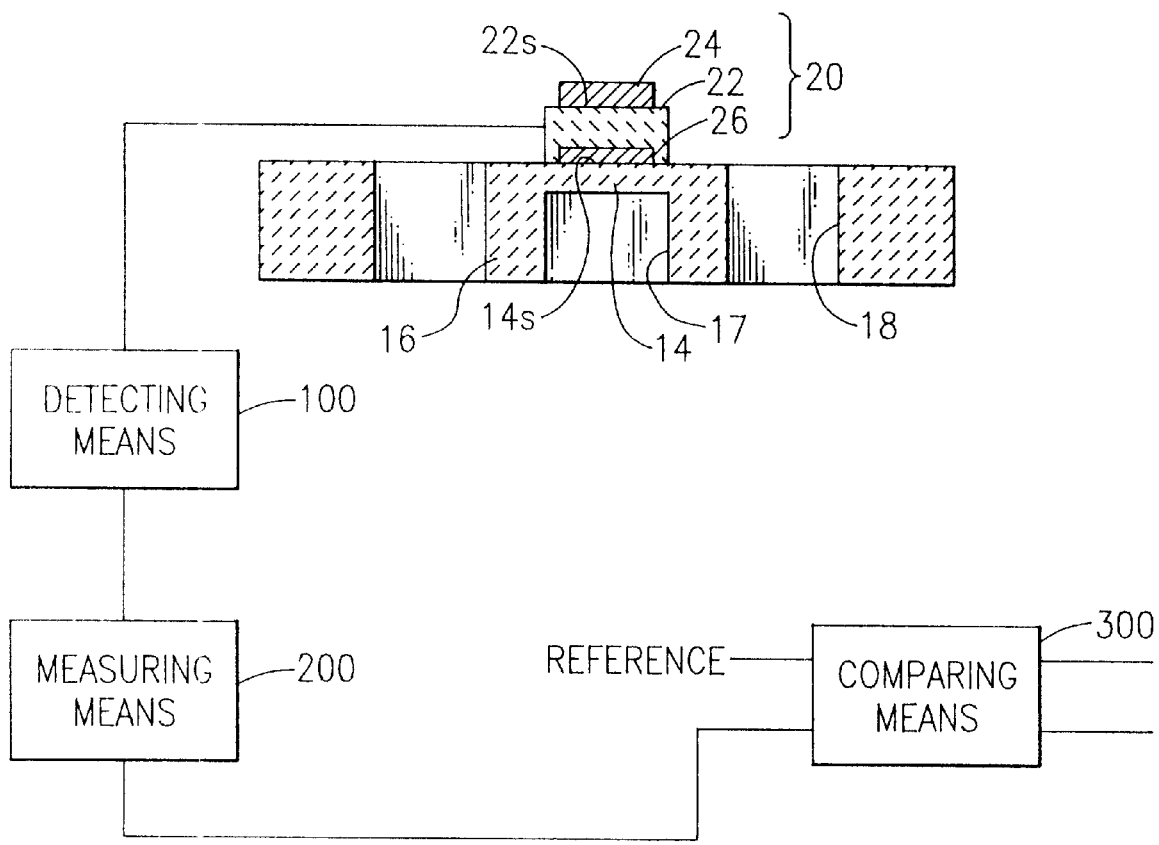

FIG. 2(a) is a plan view showing an example of the sensor element used in the first particle sensor; and FIG. 2(b) is a sectional view of the sensor element of FIG. 2(a), taken along the I—I line of FIG. 2(a). The sensor element comprises a vibrating section 14 having such a mass that is sensitive to the collision of solid particles contained in a fluid, with the vibrating section and a detecting section 20 (a convertor) for detecting the vibration of the vibrating section 14 caused by said collision and converting the vibration to electric signals.

In the present example, the vibrating section 14 is a thin plate and is fixed to a fixing section 16 so that the vibrating section 14 can vibrate, whereby the vibrating section 14 and the fixing section 16 forms a one-piece body 12. A hollow 17 is formed in the body 12 so that the vibrating section 14 can become a thin plate. On one surface 14s of the vibrating section 14 opposite to its surface facing the hollow 17 is provided a detecting section 20. In the portion of the body in the vicinity of the vibrating section 14 are formed a pair of throughholes 18 penetrating the body 12 in the thickness direction.

The vibrating section 14 need not be fixed to the fixing section 16 at the whole periphery as shown in FIG. 2, and may be fixed partially. For example, only one end of the whole periphery of the vibrating section 14 may be fixed to the fixing section 16. The hollow 17 is not restricted to such a hollow as shown in FIGS. 2(a)(b) and may be a closed space. The hollow is formed at the outlet 34 side in the example of FIG. 1, but may be formed at the inlet 32 side. As shown in FIG. 1, the detecting section 20 has a detecting surface 20s. The detecting section 20 is provided at the inlet 32 side relative to the vibrating section 14 in the example of FIG. 1, but may be provided at the outlet 34 side relative to the vibrating section 14.

There is no particular restriction as to the number, shape, etc. of the throughholes 18. However, it is preferable that one pair of the throughholes 18 have the same shape and are provided symmetrically with respect to a virtual plane penetrating the vibrating section 14 in the axial direction. The shape of the body 12 is preferably a plate, but has no particular restriction and can be appropriately determined depending upon the intended application of particle sensor.

The vibrating section 14, when collided by solid particles, vibrates, together with the vibrating section 20, in a vertical direction, i.e. a direction extending to the detecting section 20 and the hollow 17. In order to detect this vibration advantageously, the vibrating section 14 is preferably a plate. The thickness of the vibrating section 14 is preferably 1–100 $\mu$m. When the thickness is more than 100 $\mu$m, the vibrating section has a low sensitivity to collision. By contrast when the thickness is less than 1 $\mu$m, the vibrating section has low mechanical strengths.

The vibrating section 14 is preferably composed of materials which are chemically stable and which undergo no chemical change in contact with various fluids containing solid particles to be detected. The vibrating section 14 is preferably made of a ceramic such as stabilized zirconia, partially stabilized zirconia, magnesia, mullite, aluminum nitride, silicon nitride, glass, or the like. The fixing section 16 may be made of the same materials as used in the vibrating section 14, or of different materials.

The detecting section 20 has a piezoelectric film 22, a first electrode 24 and a second electrode 26 with the piezoelectric film being sandwiched between the two electrodes. The first electrode 24 covers at least part of the surface 22s of the piezoelectric film 22, and the second electrode 26 covers at least part of the surface 14s of the vibrating section 14. The piezoelectric film 22 causes, microscopically, dielectric polarization when a stress is applied thereto, and generates, macroscopically, an electric signal (e.g. electric charge or voltage) depending upon the level of the stress. At this time, it is preferable that the piezoelectric film undergoes bending displacement in the thickness direction.

The piezoelectric film 22, when the solid particles present in a fluid contact with the first electrode 24 and/or the vibrating section 14, vibrates in its thickness direction together with the vibrating section 14. This vibration applies stress to the piezoelectric film 22, whereby the piezoelectric film 22 generates electric signals. The electric signals are outputted to terminal pads by the first electrode 24 and the second electrode 26 via leads 28 and 29.

The piezoelectric film 22 has a thickness of, preferably, 1–100 $\mu$m. When the thickness is more than 100 $\mu$m, the film has a low sensitivity. However, when the thickness is less than 1 $\mu$m, the film has no sufficient reliability.

Preferably, the piezoelectric film is made of a piezoelectric ceramic. It may also be made of an electrostrictive ceramic or a ferroelectric ceramic. Alternatively it may be made of a material which needs a polarization treatment or no polarization treatment.

The ceramic used in the piezoelectric film includes, for example, a ceramic containing lead zirconate, magnesium lead niobate, nickel lead niobate, zinc lead niobate, manganese lead niobate, antimony lead stannate, lead titanate, manganese lead tungstate, cobalt lead niobate, barium titanate, or any combination thereof. For example, a ceramic composed of magnesium lead niobate, lead zirconate, and lead titanate at a ratio close to 20:37:43 has a high Curie point, is superior in piezoelectricity, and is suitable as a material for piezoelectric film.

The above ceramic may further contain an appropriate amount of an oxide of lanthanum, calcium, strontium, molybdenum, tungsten, barium, niobium, zinc, nickel, manganese, or the like; any combination of the oxides; or other compound. For example, a ceramic composed mainly of magnesium lead niobate, lead zirconate, and lead titanate, and further containing lanthanum or strontium is preferred.

The first electrode and the second electrode can have appropriate thicknesses depending upon the application of the first particle sensor, but each thicknesses is, preferably; 0.1–50 $\mu$.

The first electrode is, preferably, composed of an electroconductive metal which is a solid at room temperature. The metal includes, for example, single metals such as aluminum, titanium, chromium, iron, cobalt, nickel, copper, zinc, niobium, molybdenum, ruthenium, rhodium, silver, tin, tantalum, tungsten, iridium, platinum, gold, lead, and the like; and their alloys.

The second electrode is, preferably, composed of a high-melting metal such as platinum, ruthenium, rhodium, palladium, iridium, titanium, chromium, molybdenum, tantalum, tungsten, nickel, cobalt, or the like; or any alloy thereof. It is because the second electrode may be exposed to high temperatures when the piezoelectric film is subjected to a heat treatment and therefore the second electrode is, preferably, made of a metal resistive to a high-temperature oxidizing atmosphere. The second electrode may be made of a cermet composed of the above-mentioned high-melting metal and a ceramic such as alumina, zirconium oxide, silicon oxide, glass, or the like.

In FIG. 1, a fluid enters the housing 30 through the nozzle 33 and contacts with the vibrating section 14 and the detecting section 20 mounted on the vibrating section 14, in such a way that the fluid flow is interrupted by the contact as shown by the arrows. At this time, the solid particles present in the fluid collide with the vibrating section 14 and the detecting section 20, whereby the vibrating section 14 and the detecting section 20 vibrate. After contact with the vibrating section 14 and the detecting section 20, the fluid passes through the throughholes 18, passes through the nozzle 35, and leaves the sensor.

The first particle sensor has a basic structure as mentioned above and is further provided with: a detecting means 100 capable of detecting, from the electric signals outputted from the particle sensor, an electric signal portion having particular frequencies ranging from $\frac{1}{50}$ to 10 times the primary resonance frequency of the sensor element of the particle sensor, and a measuring means 200 capable of measuring the maximum amplitude of the detected electric signal portion.

When the first method for detecting the solid particles contained in a fluid is carried out by using the first particle sensor, first, the detecting means selectively detects, from the electric signals outputted from the particle sensor, an electric signal portion having particular frequencies ranging from $\frac{1}{50}$ to 10 times the primary resonance frequency of the sensor element of the particle sensor. Next, the measuring means 200 measures the maximum amplitude of the detected electric signal portion.

The thus-measured maximum amplitude is compared with a given value explained already in the description of the first detection method. Based on the result of the comparison, it is judged whether or not the electric signals outputted from the particle sensor are particle signals.

The detecting means 100 can be, for example, a band-pass filter capable of passing an electric signal portion having said particular frequencies. The measuring means 200 can be, for example, an oscilloscope.

The comparison of the maximum amplitude with the given value may be conducted manually, but is, preferably, conducted by an automated comparing means 300. It is possible to provide the first particle sensor further with (1) a means capable of computing the times of the electric signals (having been judged by the comparison to be particle signals) generated per unit time and (2) a means capable of issuing a warning when said times of generation per unit time have exceeded a given level. With these means, there can be easily known, for example, the degree of deterioration of engine oil (i.e. the amount of solid particles contained in engine oil) or the timing of oil change.

Then, description is made on the second method of the present invention for detecting the solid particles contained in a fluid. In the second method, it is judged whether the electric signals outputted from the particle sensor used in the method are particle signals or electric noise signals, whereby the solid particles contained in the fluid can be detected at a higher accuracy.

The particle sensor used in the second method for detecting the solid particles contained in a fluid, similarly to the particle sensor used in the first method, comprises: a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals.

Figure 5:
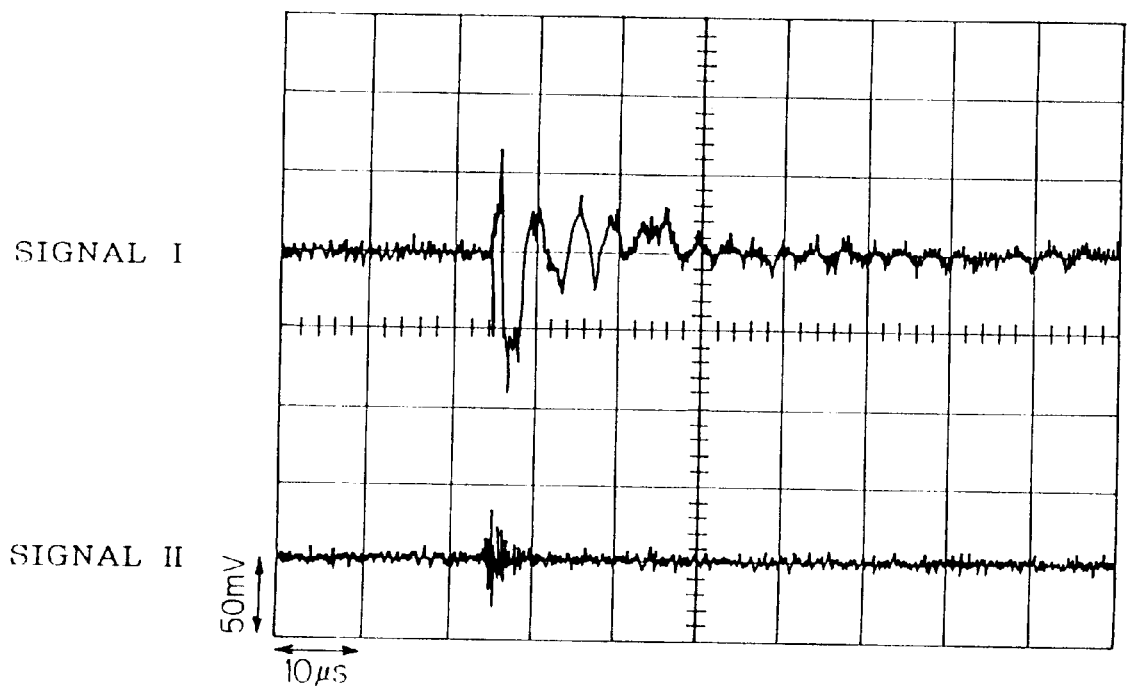
FIG. 5 shows a waveform of the electric signals (signal I) recorded after passing the electric signals (generated in the detecting section of the sensor element of the particle sensor of FIG. 1 by the collision of solid particles in a fluid, with the vibrating section of the sensor element) through a band-pass filter capable of passing electric signals having frequencies ranging from $1/50$ to 10 times the primary resonance frequency of the sensor element, and also shows a waveform of the electric signals (signal II) recorded after passing the electric signals (generated in the detecting section of the sensor element of the particle sensor of FIG. 1 by the collision of solid particles in a fluid, with the vibrating section of the sensor element) through a band-pass filter capable of passing electric signals having frequencies ranging from 2 to 10 times the primary resonance frequency of the sensor element.

FIG. 5 shows a waveform of the electric signals (signal I) recorded after passing the particle signals outputted from the above particle sensor, through a band-pass filter capable of passing electric signals having frequencies ranging from $\frac{1}{50}$ to 10 times the primary resonance frequency of the sensor element (the frequency range is hereinafter referred to as the first particular frequency range), and also shows a waveform of the electric signals (signal II) recorded after passing the particle signals outputted from the above particle sensor, through a band-pass filter capable of passing electric signals having frequencies ranging from 2 to 10 times the primary resonance frequency of the sensor element (the frequency range is hereinafter referred to as the second particular frequency range).

Figure 6:
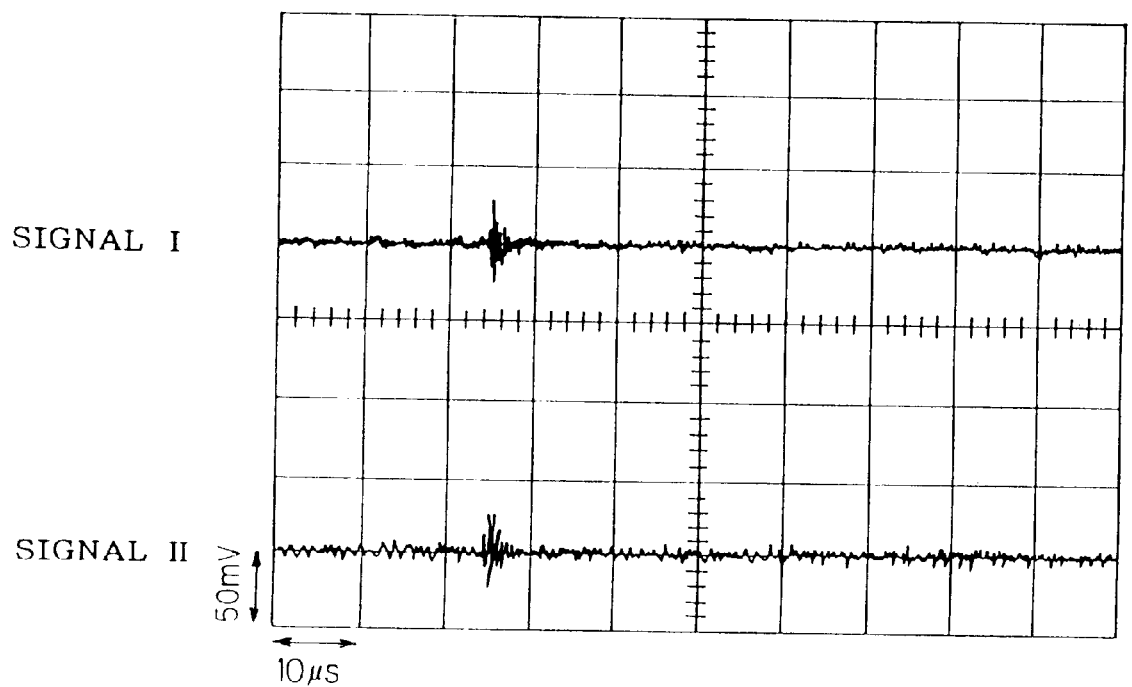
FIG. 6 shows a waveform of the electric signals (signal I) recorded after passing the electric noise signals entering the particle sensor of FIG. 1 from outside, through a band-pass filter capable of passing electric signals having frequencies ranging from $1/50$ to 10 times the primary resonance frequency of the sensor element, and also shows a waveform of the electric signals (signal II) recorded after passing the electric noise signals entering the particle sensor of FIG. 1 from outside, through a band-pass filter capable of passing electric signals having frequencies ranging from 2 to 10 times the primary resonance frequency of the sensor element.

FIG. 6 shows a waveform of the electric signals (signal I) recorded after passing the electric noise signals outputted from the above particle sensor, through a band-pass filter capable of passing electric signals having frequencies of the first particular frequency range, and also shows a waveform of the electric signals (signal II) recorded after passing the electric noise signals outputted from the above particle sensor, through a band-pass filter capable of passing electric signals having frequencies of the second particular frequency range.

As is clear from FIG. 5, the maximum amplitude of the particle signals in the first particular frequency range [i.e. the maximum amplitude (peak-to-peak) of the signal I] is considerably larger than the maximum amplitude of the particle signals in the second particular frequency range [i.e. the maximum amplitude (peak-to-peak) of the signal II]. Meanwhile, as is clear from FIG. 6, the maximum amplitude of the electric noise signals in the first particular frequency range [i.e. the maximum amplitude (peak-to-peak) of the signal I] is nearly equal to the maximum amplitude of the particle signals in the second particular frequency range [i.e. the maximum amplitude (peak-to-peak) of the signal II]. This difference between the features of the particle signals and the electric noise signals is utilized in the second method for detecting the solid particles contained in a fluid.

According to the second method a fluid to be examined is passed through the particle sensor. From the electric signals outputted from the particle sensor, an electric signal portion having the first particular frequency range is selectively detected. The maximum amplitude x of the electrical signal portion is then measured. From the electric signals outputted from the particle sensor, an electric signal portion having the second particular frequency range, is also selectively detected. The maximum amplitude Y of the electric signal portion, is then measured. When Y/X is equal to or smaller than a given value, a judgement is made whether the electric signals outputted from the particle sensor with the fluid to be examined has been caused by solid particles. The given value mentioned above must be such a value as, by comparing it with Y/X, the kind of the electric signals giving the maximum amplitudes X and Y, (i.e. particle signals or electric noise signals can be ascertained). The given value is determined based on the above-mentioned difference between the features of particle signals and electric noise signals.

As described in detail in Example 2 shown later, the experiment by the present inventors revealed that the value obtained by dividing the maximum amplitude of the particle signal portion having the second particular frequency range, by the maximum amplitude of the particle signal portion having the first particular frequency range is 0.7 or smaller. The present inventors experimentally determined that the value obtained by dividing the maximum amplitude of the electric noise signal portion having the second particular frequency range, by the maximum amplitude of the electric noise signal portion having the first particular frequency range is larger than 0.8. These two values were confirmed to be substantially constant even when the flow rate of fluid, the sizes of solid particles in fluid, etc. change.

By determining the above-mentioned given value between 0.7 and 0.8 based on the results of the above experiments, it can be judged that, when Y/X is equal to or smaller than the given value determined as above, the electric signals giving the X and Y are particle signals. By thus judging whether or not the electric signals outputted from the second particle sensor are particle signals, the solid particles contained in a fluid can be detected at a higher accuracy.

Incidentally, the first particular frequency range and the second particular frequency range, similarly to the particular frequency range in the first detection method, do not contain frequencies which become an obstacle for knowing the maximum amplitude of electric signal. Therefore, the maximum amplitude of the first particular frequency range and the maximum amplitude of the second particular frequency range can be measured accurately without being badly affected by the shifting of base line or high-frequency nose. The means for selectively detecting 100, from the electric signals outputted from the particle sensor, an electric signal portion of the first particular frequency range and an electric signal portion of the second particular frequency range for measurement of X and Y and subsequent determination of given value, can be, for example, a band-pass filter capable of passing electric signals of the first particular frequency range or the second particular frequency range.

Next, description is made on the second particle sensor of the present invention. The second particle sensor has been invented to effectively carry out the above-mentioned second method for detecting the solid particles contained in a fluid. The second particle sensor has the same basic structure as the first particle sensor the second particle sensor a first detecting means 100 capable of detecting, from the electric signals outputted from the particle sensor, an electric signal portion having the first particular frequency range, a second detecting means 100 capable of detecting, from the electric signals outputted from the particle sensor, an electric signal portion having the second particular frequency range, and a measuring means 200 capable of measuring the maximum amplitudes X and Y of the two detected electric signal portions.

In carrying out the second method for detecting the solid particles contained in a fluid, by using the second particle sensor, first, the first and second detecting means selectively detect, from the electric signals outputted from the particle sensor, an electric signal portion having the first particular frequency range and an electric signal portion having the second particular frequency range, respectively. Then, the measuring means 200 measures the maximum amplitude X of the electric signal portion having the first particular frequency range and the maximum amplitude Y of the electric signal portion having the second particular frequency range.

From the thus-measured maximum amplitudes X and Y is calculated Y/X. This Y/X is compared with a given value explained already in the description of the second detection method. Based on the result of the comparison, it is judged whether or not the electric signals outputted from the particle sensor are particle signals.

The first and second detecting means 100 can be, for example, a band-pass filter capable of passing an electric signal portion having the first or second particular frequency range. The measuring means 200 can be, for example, an oscilloscope.

The calculation of Y/X and the comparison of Y/X with the given value may be conducted manually, but is, preferably, conducted by an automated calculating and comparing means 300. It is possible to provide the second particle sensor further with (1) a means capable of computing the times of the electric signals (having been judged by the comparison to be particle signals) generated per unit time and (2) a means capable of issuing a warning when said times of generation per unit time have exceeded a given level.

The first detection method and the second detection method both of the present invention can be used as a combined detection method. This combined detection method includes the constituent features of the two detection methods. Specifically, when Y/X of the second detection method is equal to or smaller than the given value (between 0.7 and 0.8) of the second detection method, and moreover X is equal to or smaller than C (given value) of the first detection method, the electric signals giving the X and Y are judged to be particle signals. Thereby, particle signals can be distinguished from turbulent flow signals and electric noise signals, in one step.

In order to effectively carry out such a combined detection method, the first particle sensor and the second particle sensor can be used as a combined particle sensor which includes the constituent elements of the two particle sensors. A specific example of the combined particle sensor can be such a particle sensor having, besides the basic structure of the first and second particle sensors, the first and second detecting means 100 and measuring means 300 of the second particle sensor, along with the comparing means of the first particle sensor and the calculating and comparing means 300 of the second particle sensor.

The above combined particle sensor can further have a means capable of, when the calculating and comparing means 300 of the second particle sensor has indicated that Y/X is equal to or smaller than the given value (between 0.7 and 0.8) of the second detection method and further when the comparing means 300 of the first particle sensor has indicated that X is equal to or smaller than the given value C of the first detection method, computing the times of electric signals (giving such X and Y) generated per unit time, and a means capable of issuing a warning when said times of electric signals generated per unit time has exceeded a given level.

Next, description is made on the process for producing the sensor element used in the first and second particle sensors of the present invention.

The body of the sensor element is made in one piece by laminating a plurality of laminating layers (which are green sheets or green tapes) by hot pressing or the like and then sintering the laminate. For example, in the body 12 of FIG. 2, two laminating layers of green sheets or green tapes are laminated; before the lamination, a throughhole of desired shape to become a hollow 17 is formed in the second layer. Alternatively, the layers may be formed by pressure molding, casting, injection molding, or the like and the hollow may be formed by cutting, machining, laser processing, punching by pressing, or the like. Although the laminating layers need not have the same thickness, it is preferred that the layers undergo similar shrinkages in sintering.

Formation of a detecting section 20 on the ceramic vibrating section 14 can be conducted as follows. A piezoelectric is formed by pressing a mold or by tape forming using a material slurry. Before sintering sintering is laminated on the vibrating section of the body before sintering by hot pressing, and sintering is conducted to form a body and a piezoelectric. In this case, electrodes must be formed on the body or the piezoelectric beforehand by a film forming method described later.

Although the sintering temperature for the piezoelectric film is determined appropriately depending upon the materials of the film, the sintering temperature is generally 800–1,400° C., preferably 1,000–1,400° C. In this case, it is preferred for controlling the composition of the piezoelectric film to conduct sintering in the presence of the evaporation source of the components of the piezoelectric film.

In the film forming method, a second electrode 26, a piezoelectric film 22, and a first electrode 24 are laminated in this order on the vibrating section 14 to form a detecting section 20. As the film forming method, there can be appropriately used any known forming method. For example, a thick film method (e.g. screen printing), a coating method (e.g. dipping), or a thin film method [e.g. ion beam, sputtering, vacuum deposition, ion plating, chemical vapor deposition (CVD), or plating]. However, the film forming method is not restricted to these methods. Among these methods, screen printing is preferred because of stable production.

A second electrode 26, leads 28 and 29, and terminal pads can be simultaneously formed by screen printing. A piezoelectric film 22 is, preferably, formed by screen printing, dipping, or the like. In these methods, a piezoelectric film can be formed on the body using a paste or a slurry each containing materials for piezoelectric film and composed mainly of ceramic particles, whereby the piezoelectric film can have good properties.

When a piezoelectric film is formed by a film forming method, since the detecting section and the vibrating section can be bonded integrally without using any adhesive, this method is, especially, preferred because of the high reliability, reproducibility, and integratability. A piezoelectric film may be formed in an appropriate pattern. The pattern may be formed by screen printing, photolithography, or the like, or may be formed by removing unnecessary portions using mechanical processing such as laser processing, slicing, ultrasonic processing, or the like.

Each film (22, 24, and 26) thus formed on the body may be made integral with the body by heat treatment each time one film is formed, or by heat-treating these films simultaneously after formation of all films. When the first and second electrodes are formed by a thin film method, heat treatment is not always necessary for their integration.

Throughholes 18 may be formed in the green sheets or green tapes or in the laminating layers obtained using a mold, at the time of body formation, by mechanical processing such as cutting, grinding, punching by pressing, or the like. That is, green sheets or the like may be machined so as to form throughholes of desired shape. Throughholes may also be formed by mechanical processing such as laser processing, cutting, ultrasonic processing, or the like, after sintering of the body. Throughholes may also be formed after forming a detecting section, using the same processing method.

The present invention is described in more detail below with reference to examples. However, the present invention is not restricted to these examples.

EXAMPLE 1

There was produced a particle sensor which had a basic structure shown in FIG. 1 and which comprised a sensor element 10 having a primary resonance frequency of 320 kHz. The sensor element 10 comprised a body 12 of 0.3 mm in thickness, made of partially stabilized zirconia. The body 12 comprised a vibrating section 14 of 10 $\mu$m in thickness, made of partially stabilized zirconia. In the body were formed two throughholes 18 of rectangular shape (2 mm×1.5 mm) in the vicinity of the vibrating section 14. The sensor element 10 further comprised, as shown in FIGS. 2(*a*)(*b*), a piezoelectric film 22 of 20 $\mu$m in thickness, composed mainly of magnesium lead niobate, lead zirconate, and lead titanate, and further containing lanthanum and strontium; a first electrode 24 of 0.3 $\mu$m in thickness, made of gold; and a second electrode 26 of 5 $\mu$m in thickness, made of platinum.

Considering a case of applying the above-produced particle sensor in the lubricating oil system of a large-sized diesel engine having a displacement of 10,000 cc and an engine oil flow rate of 150 l/min, there was determined, for the particle sensor, a given value (which is C explained previously and necessary for distinguishing the particle signals outputted from the particle sensor, from the turbulent flow signals also outputted from the particle sensor), according to the following procedure.

First, investigation was made on the conditions to be used in applying the particle sensor in the above usage, (i.e. the flow rate of a fluid) to be passed through the particle sensor and the sizes of the solid particles to be contained in the fluid. In applying a particle sensor in the lubricating oil system of a diesel engine, the particle sensor is generally provided in a bypass formed in parallel to the oil path. In this case, the flow rate of an oil portion which can be passed through the bypass without impairing the lubrication of engine, is about 1–2% of the total oil flow rate, i.e. about 1.5–3 l/min in the case of the above diesel engine. Also in the lubricating oil system of a diesel engine, an oil filter is generally provided to remove the particles of about 20–50 $\mu$m in size, contained in the lubricating oil. Therefore, the sizes of the particles in the oil passing through the particle sensor are 50 $\mu$m or less.

In the present example, referring to such conditions to be used in applying the particle sensor in a diesel engine such as mentioned above, an engine oil containing metal particles of 25–44 $\mu$m in size was passed through the above-produced particle sensor at a flow rate of 2.3 l/min. In this condition, particle signals were outputted from the particle sensor and measured for the maximum amplitude. For easy and accurate measurement, the signals outputted were amplified 100-fold by the use of an amplifier. The amplified signals were passed through a band-pass filter capable of passing a signal portion having frequencies of 1/50 (6.4 kHz) to 10 times (3,200 kHz) the primary resonance frequency (320 kHz) of the sensor element. This eliminated the shifting of the base line of the signals output from the particle sensor, caused by the variation of oil flow rate, etc. and also reduced high-frequency noise. Thus, particle signals were obtained 1,000 times and the maximum amplitudes (peak-to-peak) thereof were measured. The results (distribution of times of maximum amplitudes) are shown in Table 1 and FIG. 8.

TABLE 1

| Maximum amplitude (V) | Times |
| --- | --- |
| 0.00 < maximum amplitude ≦ 0.02 | 0 |
| 0.02 < maximum amplitude ≦ 0.04 | 0 |
| 0.04 < maximum amplitude ≦ 0.04 | 3 |

TABLE 1-continued

| Maximum amplitude (V) | Times |
|---|---|
| 0.06 < maximum amplitude ≦ 0.04 | 18 |
| 0.08 < maximum amplitude ≦ 0.04 | 69 |
| 0.10 < maximum amplitude ≦ 0.04 | 114 |
| 0.12 < maximum amplitude ≦ 0.04 | 153 |
| 0.14 < maximum amplitude ≦ 0.04 | 145 |
| 0.16 < maximum amplitude ≦ 0.04 | 117 |
| 0.18 < maximum amplitude ≦ 0.04 | 99 |
| 0.20 < maximum amplitude ≦ 0.04 | 69 |
| 0.22 < maximum amplitude ≦ 0.04 | 52 |
| 0.24 < maximum amplitude ≦ 0.04 | 40 |
| 0.26 < maximum amplitude ≦ 0.04 | 31 |
| 0.28 < maximum amplitude ≦ 0.04 | 21 |
| 0.30 < maximum amplitude ≦ 0.04 | 20 |
| 0.32 < maximum amplitude ≦ 0.04 | 19 |
| 0.34 < maximum amplitude ≦ 0.04 | 13 |
| 0.36 < maximum amplitude ≦ 0.04 | 13 |
| 0.38 < maximum amplitude ≦ 0.04 | 4 |
| 0.40 < maximum amplitude ≦ 0.04 | 0 |
| 0.42 < maximum amplitude ≦ 0.04 | 0 |
| Total | 1000 |

Figure 8:
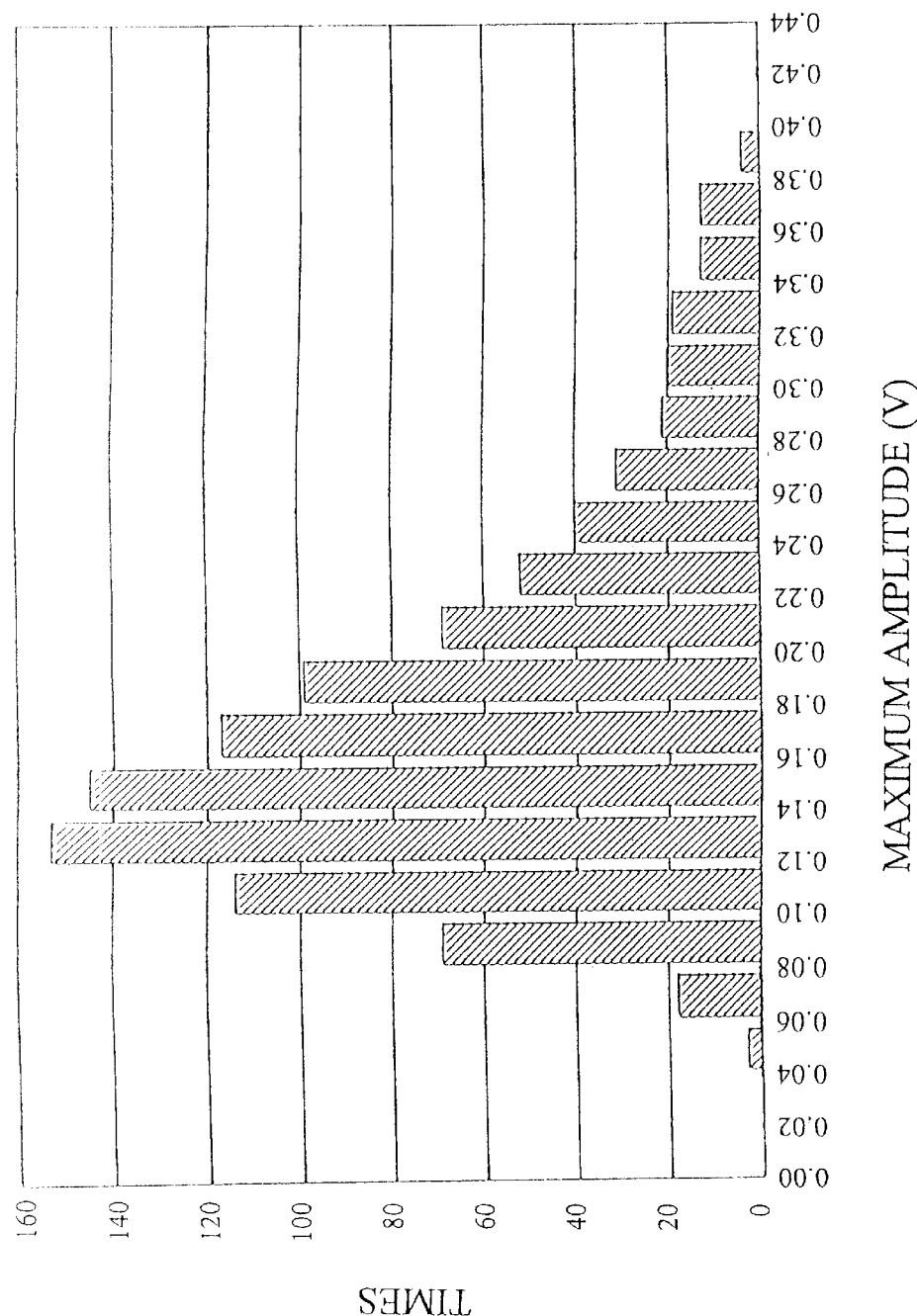
FIG. 8 is a graph showing the results obtained in Example 1.

As is clear from Table 1 and FIG. 8, the largest amplitude of 1,000 times of the electric signals was 0.4 V under the conditions of the present example. Using the same particle sensor under the same conditions except that the engine oil contained no particles, turbulent flow signals were obtained and the maximum amplitudes thereof were measured. The maximum amplitudes were always 1 V or higher. These results indicate that, in applying the particle sensor produced above, in the lubricating oil system of the above-mentioned diesel engine, the given value can be determined to be at least equal to 0.4 V and smaller than 1 V when the amplification of signals is set 100-fold. When the electric signals are obtained with the particle sensor and the maximum amplitude of a portion of the signals having frequencies of 6.4 to 3,200 kHz is equal to or smaller than the given value, the electric signals can be judged to be particle signals.

EXAMPLE 2

Through the same particle sensor as used in Example 1 was passed through an engine oil containing metal particles of 25–44 μm in size, at a flow rate of 2.3 l/min, to allow the particle sensor to output particle signals. Also, the same engine oil containing no metal particles was passed through the same particle sensor at the same flow rate in a steady state of low turbulent flow and observation was made over a long period of time. In this condition, electric noise signals were outputted from the particle sensor.

The outputted particle signals and electric noise signals were amplified 100-fold by the use of an amplifier. The amplified signals were passed through a first band-pass filter capable of passing an electric signal portion having frequencies of 1/50 (6.4 kHz) to 10 times (3,200 kHz) the primary resonance frequency (320 kHz) of the particle sensor, and also through a second band-pass filter capable of passing an electric signal portion having frequencies of 2 (640 kHz) to 10 times (3,200 kHz) the primary resonance frequency (320 kHz) of the particle sensor. Thus, 1,000 particle signals and 1,000 electric noise signals were obtained. For each of them, there were measured the maximum amplitude X after passing through the first band-pass filter and the maximum amplitude Y after passing through the second band-pass filter, after which Y/X was determined by calculation. The results (distribution of times of Y/X) are shown in Table 2 and FIG. 9.

TABLE 2

| | Times | |
|---|---|---|
| Y/X | Particle signal | Electric noise signal |
| 0.00 < Y/X ≦ 0.05 | 0 | 0 |
| 0.05 < Y/X ≦ 0.10 | 0 | 0 |
| 0.10 < Y/X ≦ 0.15 | 2 | 0 |
| 0.15 < Y/X ≦ 0.20 | 37 | 0 |
| 0.20 < Y/X ≦ 0.25 | 51 | 0 |
| 0.25 < Y/X ≦ 0.30 | 110 | 0 |
| 0.30 < Y/X ≦ 0.35 | 186 | 0 |
| 0.35 < Y/X ≦ 0.40 | 196 | 0 |
| 0.40 < Y/X ≦ 0.45 | 158 | 0 |
| 0.45 < Y/X ≦ 0.50 | 129 | 0 |
| 0.50 < Y/X ≦ 0.55 | 81 | 0 |
| 0.55 < Y/X ≦ 0.60 | 36 | 0 |
| 0.60 < Y/X ≦ 0.65 | 12 | 0 |
| 0.65 < Y/X ≦ 0.70 | 2 | 0 |
| 0.70 < Y/X ≦ 0.75 | 0 | 0 |
| 0.75 < Y/X ≦ 0.80 | 0 | 0 |
| 0.80 < Y/X ≦ 0.85 | 0 | 19 |
| 0.85 < Y/X ≦ 0.90 | 0 | 82 |
| 0.90 < Y/X ≦ 0.95 | 0 | 169 |
| 0.95 < Y/X ≦ 1.00 | 0 | 730 |
| Total | 1000 | 1000 |

As is clear from Table 2 and FIG. 9, even the largest of the Y/Xs of the particle signals was 0.7. Also, even the smallest of the Y/Xs of the electric noise signals exceeded 0.8. From the above results, the given value can be determined between 0.7 and 0.8. When electric signals are obtained with the particle sensor and the Y/X thereof is equal to or smaller than the given value, the electric signals can be judged to be particle signals. Incidentally, in Example 2, nearly the same results were obtained even when the particle sensor was used under different conditions.

As described herein, the present method can judge whether the electric signals outputted from the present particle sensor are signals caused by the collision of solid particles with the sensor, or signals caused by other reasons (signals caused by the turbulent flow of fluid and electric noise signals entering the particle sensor from outside). Therefore, the present method can reduce the risk of taking particle signals for other signals and can increase the accuracy of detection of solid particles. Further, the present method can be effectively carried out by the use of the present particle sensor.

What is claimed is:

1. A method for detecting the solid particles contained in a fluid, by the use of a particle sensor comprising:

a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals, which method comprises steps of:

passing a fluid to be examined, through the particle sensor, selectively detecting, from the electric signals outputted from the particle sensor, an electric signal portion having particular frequencies ranging from 1/50 to 10 times the primary resonance frequency of the sensor element, measuring the maximum amplitude of said electric signal portion, comparing the maximum amplitude measured above, with a given value predetermined with the particle sensor based on (1) the maximum amplitude of a portion of the electric signals caused by the collision of solid particles contained in a fluid, having the above particular frequencies and (2) the maximum amplitude of a portion of the electric signals caused by the turbulent flow of the same fluid containing no solid particles, having the above particular frequencies, and judging, depending upon the result of the above comparison, whether or not the electric signals outputted from the particle sensor with the fluid to be examined have been caused by the collision of solid particles with the particle sensor.

2. A method according to claim 1, wherein the given value is predetermined so as to satisfy the following formula:

$$A \leq C < B$$

C is the given value; A is the largest amplitude of a plurality of maximum amplitudes obtained when electric signals are generated a plurality of times by colliding solid particles in a fluid, with the particle sensor, a portion of said electric signals having said particular frequencies is selectively detected for each collision, and the maximum amplitude is measured for each collision; and B is the smallest amplitude of a plurality of maximum amplitudes obtained when electric signals are generated a plurality of times by allowing a turbulent flow to occur in a fluid and allowing the turbulent flow to hit against the particle sensor, a portion of said electric signals having said particular frequencies is selectively detected for each hitting, and the maximum amplitude is measured for each hitting, and wherein the electric signals outputted from the element sensor with the fluid to be examined are judged to have been caused by the collision of solid particles when the maximum amplitude of a portion of said electric signals having said particular frequencies is equal to or smaller than said given value C.

3. A particle sensor comprising:

a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals, which particle sensor is provided with:

a detecting means capable of detecting, from the electric signals outputted from the element sensor, an electric signal portion having particular frequencies ranging from 1/50 to 10 times the primary resonance frequency of the sensor element of the particle sensor, and a measuring means capable of measuring the maximum amplitude of the detected electric signal portion.

4. A particle sensor according to claim 3, which is further provided with:

a comparing means capable of comparing the maximum amplitude measured by the measuring means, with a given value.

5. A method for detecting the solid particles contained in a fluid, by the use of a particle sensor comprising:

a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals, which method comprises steps of:

passing a fluid to be examined, through the particle sensor, selectively detecting, from the electric signals outputted from the sensor element, an electric signal portion having particular frequencies ranging from 1/50 to 10 times the primary resonance frequency of the sensor element, and measuring the maximum amplitude X of said electric signal portion, also selectively detecting, from the electric signals outputted from the particle sensor, an electric signal portion having particular frequencies ranging from 2 to 10 times the primary resonance frequency of the sensor element, and measuring the maximum amplitude Y of said electric signal portion, and judging, when Y/X is equal to or smaller than a given value, that the electric signals outputted from the particle sensor with the fluid to be examined has been caused by solid particles.

6. The method according to claim 5, wherein the given value is determined in a range of 0.7 to 0.8.

7. A particle sensor comprising:

a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals, which particle sensor is provided with:

a first detecting means capable of detecting, from the electric signals outputted from the sensor element, an electric signal portion having particular frequencies ranging from 1/50 to 10 times the primary resonance frequency of the sensor element of the particle sensor, a second detecting means capable of detecting, from the electric signals outputted from the particle sensor, an electric signal portion having particular frequencies ranging from 2 to 10 times the primary resonance frequency of the sensor element, and amplitudes of said two electric signal portions.

8. A particle sensor according to claim 7, which is further provided with a calculating and comparing means capable of dividing the maximum amplitude of the electric signal portion having particular frequencies ranging from 2 to 10 times the primary resonance frequency of the sensor element, by the maximum amplitude of the electric signal portion having particular frequencies ranging from 1/50 to 10 times the primary resonance frequency of the sensor element, and comparing the resulting quotient with a given value.

* * * * *